United States Patent
Coates et al.

(10) Patent No.: US 11,498,915 B2
(45) Date of Patent: Nov. 15, 2022

(54) TRKA INHIBITOR

(71) Applicant: Eli Lilly and Company, Indianapolis, IN (US)

(72) Inventors: David A. Coates, New Palestine, IN (US); Ryan James Linder, Carmel, IN (US); Laia Malet-Sanz, Twickenham (GB)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 17/328,459

(22) Filed: May 24, 2021

(65) Prior Publication Data
US 2021/0371399 A1  Dec. 2, 2021

Related U.S. Application Data

(60) Provisional application No. 63/031,073, filed on May 28, 2020.

(51) Int. Cl.
*C07D 401/14* (2006.01)
(52) U.S. Cl.
CPC ........ *C07D 401/14* (2013.01); *C07B 2200/13* (2013.01)
(58) Field of Classification Search
CPC .......................... C07D 401/14; C07B 2200/13
See application file for complete search history.

(56) References Cited

U.S. PATENT DOCUMENTS 9,328,096 B2 * 5/2016 Bagal ..................... A61P 35/00
9,815,846 B2   11/2017 Mitchell et al.

FOREIGN PATENT DOCUMENTS

| WO | 2015/143652 A1 | 10/2015 |
|---|---|---|
| WO | 2015/143653 A1 | 10/2015 |
| WO | 2015/143654 A1 | 10/2015 |
| WO | 2015/148344 A2 | 10/2015 |

OTHER PUBLICATIONS

International Searching Authority, International Search Report, and Search Strategy for PCT/US2021/033853, WO, A1, dated May 24, 2021, Eli Lilly and Company.
Written Opinion of the International Searching Authority for PCT/US2021/033853, WO, A1, dated May 24, 2021, Eli Lilly and Company.

* cited by examiner

*Primary Examiner* — Timothy R Rozof
(74) *Attorney, Agent, or Firm* — Quarles & Brady LLP

(57) ABSTRACT

The present invention relates to compound of the following structure for use as an inhibitor of TrkA, as well as compositions including this compound, and methods of using this compound for the treatment of pain including post-surgical pain, rheumatoid arthritis pain, neuropathic pain and osteoarthritis pain.

21 Claims, No Drawings

TRKA INHIBITOR

The present invention is in the field of medicine. Particularly, the present invention relates to a compound that inhibits tropomysin receptor kinase A (TrkA), compositions comprising such a compound, and methods of using such a compound for the treatment of pain. The compound, and methods of using the same may treat acute or chronic pain of nociceptive/inflammatory, neuropathic, nociplastic, or mixed etiologies.

U.S. Patent Application Publication No. 2013/0336964 explains the role of TrkA and Nerve Growth Factor (NGF) in the human pain system. Accordingly, targeting and inhibiting TrKA can potentially be useful in treating pain. (See, for example, WO 2015/15148344; WO 2015/143652; WO 2015/143653; WO 2015/143654; WO 2015/159175; and WO 2015/170208). Antibodies have also been developed that are designed to bind to and/or inhibit TrkA and treat pain. (See, for example, U.S. Pat. No. 10,618,974, U.S. Patent Application Publication No. 2013/0336961, U.S. Pat. No. 7,601,818, WO 2000/73344 and WO 2016/087677). The protein sequence for human TrkA is provided in U.S. Patent Application Publication No. 2013/0336961.

Persistent pain represents a major health problem and causes significant losses in quality of life. Persistent pain may present with different levels of severity, and is associated with a variety of pathologies, such as back injury or degenerative disk disease, migraine headaches, arthritis, diabetic neuropathy, cancer and other diseases. Mild pain is presently treated with acetaminophen, aspirin, and other (typically over-the-counter) medications. Moderate pain may be controlled using corticosteroidal drugs such as cortisol and prednisone. Problems with the effectiveness and/or tolerability of existing treatments are well known, and corticosteroids for example display remarkable adverse effects including weight gain, insomnia, and immune system weakening. Moderate or severe pain may be treated with opioids such as morphine and fentanyl, but long-term use of opiates is limited by several serious drawbacks, including development of addiction, tolerance and physical dependence. Potential overuse of opioids has been characterized as an "opioid epidemic" in view of the growing number of people that use and may be addicted to opioids.

As current pain therapies are often poorly effective and/or have serious undesirable side effects (like addiction), an urgent need exists to develop drugs which are directed to new molecular targets. Specifically, there is an urgent medical need to develop new pain treatment agents that are less likely to be addictive and/or cause dependency. Further, there is a need for new TrkA inhibitors that may provide one or more improved pharmacological properties, for example safety, potency, efficacy, or tolerability, in particular for the treatment of pain/chronic pain. To date, no agents targeting TrkA signaling have been approved for the treatment of pain. Thus, there remains a need for agents that can inhibit TrkA signaling, such as alternative TrkA inhibitors.

The present embodiments provide a compound that is a TrkA inhibitor useful in the treatment of pain. Specifically, an embodiment of the present invention provides a TrkA inhibitor compound of the formula (which is designated as "FORMULA I"):

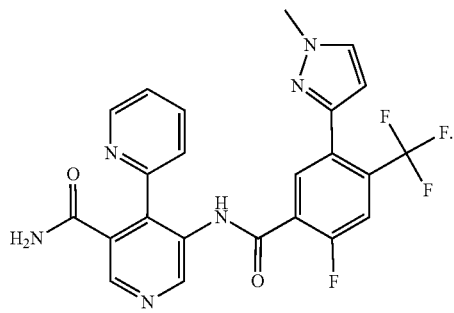

In addition to the compound of FORMULA I, embodiments of the present invention provide one or more pharmaceutically acceptable salts of the compound of FORMULA I, and the use of said salts as TrKA inhibitors.

An embodiment of the present invention further provides use of a pharmaceutical composition comprising a compound of FORMULA I or a pharmaceutically salt thereof for use in the treatment of pain. The pharmaceutical compositions may include the compound or pharmaceutically acceptable salt of FORMULA I, and one or more pharmaceutically acceptable carriers, diluents or excipients.

An embodiment of the present invention further provides the use of a pharmaceutical composition comprising the compound of FORMULA I, or pharmaceutically acceptable salt thereof, for use in the treatment of pain.

An embodiment of the present invention further provides a method of treating pain upon administration to a patient thereof. Specifically, the present embodiments provide a method for treating pain comprising administering to a patient in need thereof an effective amount of a compound of FORMULA I, or pharmaceutically acceptable salt thereof, or a pharmaceutical composition thereof. In another embodiment, the present methods provide a compound of FORMULA I, or a pharmaceutically acceptable salt thereof, or a pharmaceutical composition thereof, for treating acute or chronic pain that is musculoskeletal or neuropathic in origin. Specific, non-limiting examples of pain include, post-surgical pain, rheumatoid arthritis pain, osteoarthritis pain, neuropathic pain, diabetic nerve pain (DNP), chronic lower back pain (CLBP), including non radicular (non-neuropathic) and radicular lower back pain (which are sometimes referred to as lumbosacral radiculopathy (LSR) or sciatica), as well as visceral pain such as chronic prostatitis, interstitial cystitis (bladder pain) or chronic pelvic pain.

An embodiment of the present invention provides the compound of FORMULA I, or a pharmaceutically acceptable salt thereof, or a pharmaceutical composition thereof, for use in therapy. Another embodiment provides a compound of FORMULA I, or a pharmaceutically acceptable salt thereof, for use in the treatment pain. In some embodiments, the pain is acute or chronic pain that is musculoskeletal or neuropathic in origin. Specific, non-limiting examples of pain include post-surgical pain, rheumatoid arthritis pain, osteoarthritis pain, neuropathic pain, DNP, and CLBP, including non radicular (non-neuropathic) and radicular lower back pain (which are sometimes referred to as LSR or sciatica), as well as visceral pain (such as, for example, chronic prostatitis, interstitial cystitis (bladder pain) or chronic pelvic pain).

Further, the present embodiments provide the use of a compound of FORMULA I or pharmaceutically acceptable salts thereof of a pharmaceutical composition thereof in the manufacture of a medicament for the treatment of pain. In some embodiments, the pain may be acute or chronic pain that is musculoskeletal or neuropathic in origin. Specific, non-limiting examples of pain include, post-surgical pain, rheumatoid arthritis pain, osteoarthritis pain, neuropathic pain, DNP, and CLBP, including non radicular (non-neuropathic) and radicular lower back pain (which are sometimes referred to as LSR or sciatica), as well as visceral pain, such as chronic prostatitis, interstitial cystitis (bladder pain) or chronic pelvic pain).

The present embodiments also provide a compound that is the hemisuccinic acid salt of the compound of FORMULA I.

In addition, some embodiments have the hemisuccinic acid salt of the compound of FORMULA I be crystalline. In some embodiments, the hemisuccinic acid salt is characterized by a substantial peak in the X-ray diffraction spectrum, at diffraction angle 2-theta of 10.5° in combination with one or more of the peaks selected from the group consisting of 12.6, and 22.2; with a tolerance for the diffraction angles of 0.2 degrees.

An embodiment of the present invention further provides use of a pharmaceutical composition comprising the hemisuccinic acid salt of FORMULA I for use in the treatment of pain. The pharmaceutical compositions may include the hemisuccinic acid salt of FORMULA I, and one or more pharmaceutically acceptable carriers, diluents or excipients.

An embodiment of the present invention further provides the use of a pharmaceutical composition comprising the hemisuccinic acid salt of FORMULA I for use in the treatment of pain.

An embodiment of the present invention further provides a method of treating pain upon administration to a patient thereof. Specifically, the present embodiments provide a method for treating pain comprising administering to a patient in need thereof an effective amount of the hemisuccinic acid salt of FORMULA I, or a pharmaceutical composition thereof. In another embodiment, the present methods provide the hemisuccinic acid salt of FORMULA I, or a pharmaceutical composition thereof, for treating acute or chronic pain that is musculoskeletal or neuropathic in origin. Specific, non-limiting examples of pain include, post-surgical pain, rheumatoid arthritis pain, osteoarthritis pain, neuropathic pain, diabetic nerve pain (DNP), chronic lower back pain (CLBP), including non radicular (non-neuropathic) and radicular lower back pain (which are sometimes referred to as lumbosacral radiculopathy (LSR) or sciatica), as well as visceral pain such as chronic prostatitis, interstitial cystitis (bladder pain) or chronic pelvic pain.

An embodiment of the present invention provides the hemisuccinic acid salt of FORMULA I, or a pharmaceutical composition thereof, for use in therapy. Another embodiment provides the hemisuccinic acid salt of FORMULA I, for use in the treatment pain. In some embodiments, the pain is acute or chronic pain that is musculoskeletal or neuropathic in origin. Specific, non-limiting examples of pain include post-surgical pain, rheumatoid arthritis pain, osteoarthritis pain, neuropathic pain, DNP, and CLBP, including non radicular (non-neuropathic) and radicular lower back pain (which are sometimes referred to as LSR or sciatica), as well as visceral pain (such as, for example, chronic prostatitis, interstitial cystitis (bladder pain) or chronic pelvic pain).

Further, the present embodiments provide the use of the hemisuccinic acid salt of FORMULA I or a pharmaceutical composition thereof in the manufacture of a medicament for the treatment of pain. In some embodiments, the pain may be acute or chronic pain that is musculoskeletal or neuropathic in origin. Specific, non-limiting examples of pain include, post-surgical pain, rheumatoid arthritis pain, osteoarthritis pain, neuropathic pain, DNP, and CLBP, including non radicular (non-neuropathic) and radicular lower back pain (which are sometimes referred to as LSR or sciatica), as well as visceral pain, such as chronic prostatitis, interstitial cystitis (bladder pain) or chronic pelvic pain).

An effective amount can be determined by one skilled in the art by the use of known techniques, and by observing results obtained under analogous circumstances. In determining the effective amount for a patient, a number of factors are considered, including, but not limited to: weight, age, and general health; the specific disease or disorder involved; the degree of involvement or severity of the disease or disorder; the response of the individual patient; the compound administered; the mode of administration; the bioavailability characteristics of the preparation administered; the dose regimen selected; the use of concomitant medication; and other relevant circumstances.

The compound of the present invention may be formulated as pharmaceutical compositions administered by any route which makes the compound bioavailable. Preferably, such compositions are for oral administration. Such pharmaceutical compositions and processes for preparing the same are well known in the art (See, e.g., Remington: The Science and Practice of Pharmacy, L. V. Allen, Editor, $22^{nd}$ Edition, Pharmaceutical Press, 2012).

The compound and pharmaceutically acceptable salts of the present embodiments are expected to treat a class of pain, which includes post-surgical pain, neuropathic pain, rheumatoid arthritis pain and osteoarthritis pain, including, for example, non radicular (non-neuropathic) and radicular CLBP, DNP, and LSR. The compound of FORMULA I and pharmaceutically acceptable salts or pharmaceutical compositions thereof of the present invention may also be useful in the treatment of other forms of pain. As used interchangeably herein, "treatment" and/or "treating" and/or "treat" are intended to refer to all processes wherein there may be a slowing, interrupting, arresting, controlling, stopping, or reversing of the progression of the disorders described, but does not necessarily indicate a total elimination of all disorder symptoms. Treatment may also include the prevention of pain. Treatment includes administration of a compound of FORMULA I, or a pharmaceutically acceptable salt thereof or pharmaceutical composition thereof, for treatment of a disease or condition in a human that would benefit from a reduction in TrkA activity, wherein said treatment provides: (a) inhibiting further progression of the disease, i.e., arresting its development; (b) relieving the disease, i.e., causing regression of the disease or disorder or alleviating symptoms or complications thereof; and/or (c) preventing the onset of the disease of symptoms. Treatment, as used herein, expressly includes reducing incidence of pain, ameliorating a pain or one or more symptoms of a pain, palliating a pain or one or more symptoms of a pain, delaying the development of pain. Treatment also includes, in some situations, treating the pain but not necessarily modifying the underlying disease or condition giving rise to the pain.

"Reducing incidence" of pain as used herein means any of reducing duration, and/or frequency of pain (including, for example, delaying or increasing time to post-surgical pain in an individual). As is understood by those skilled in the art, individuals may vary in terms of their response to treatment, and as such, a "method of reducing incidence of rheumatoid arthritis pain or osteoarthritis pain in an individual" reflects administering the compound or pharmaceutically acceptable salts based on a reasonable expectation that such administration is likely cause a reduction in incidence in that particular individual.

Treatment of pain also includes reducing the severity of the pain as well as reducing the need for and/or amount of (e.g., exposure to) other drugs and/or therapies generally used for this conditions, including, for example, opiates).

"Ameliorating" a pain or one or more symptoms of a pain (such as rheumatoid arthritis pain or osteoarthritis pain) means a lessening or improvement of one or more symptoms of pain, as compared to not administering a compound or pharmaceutically acceptable salt. "Ameliorating" includes shortening or reduction in duration of a symptom.

"Palliating" pain or one or more symptoms of a pain (such as rheumatoid arthritis pain or osteoarthritis pain) means lessening the extent of one or more undesirable clinical manifestations of post-surgical pain in an individual, or population of individuals, treated with a compound or pharmaceutically acceptable salt in accordance with the invention.

As used herein, "delaying" the development of pain means to defer, hinder, slow, retard, stabilize, and/or postpone progression of pain, such as post-surgical pain, rheumatoid arthritis pain, or osteoarthritis pain. Such a delay can be of varying lengths of time, depending on the history of the disease and/or individuals being treated. As is evident to one skilled in the art, a sufficient or significant delay can, in effect, encompass prevention, in that the individual does not develop pain. A method that "delays" development of the symptom can be a method that reduces probability of developing the symptom in a given time frame, and/or reduces the extent of the symptoms in a given time frame, when compared to not using the method. Such comparisons are typically based on clinical studies, using a statistically significant number of subjects.

"Pain" as used herein refers to pain of any etiology, including acute and chronic pain, and any pain with an inflammatory component. Examples of pain include post-surgical pain, post-operative pain (including dental pain), migraine, headache and trigeminal neuralgia, pain associated with burn, wound or kidney stone, pain associated with trauma (including traumatic head injury), neuropathic pain, pain associated with musculo-skeletal disorders such as rheumatoid arthritis, osteoarthritis, including, for example, non radicular (non-neuropathic) and radicular CLBP, DNP, and LSR (sciatica), ankylosing spondylitis, sero-negative (non-rheumatoid) arthropathies, non-articular rheumatism and peri-articular disorders, and pain associated with cancer (including "break-through pain" and pain associated with terminal cancer), peripheral neuropathy and post-herpetic neuralgia. Examples of pain with an inflammatory component (in addition to some of those described above) include rheumatic pain, pain associated with mucositis, and dysmenorrhea.

Pain, as defined herein, expressly includes chronic pain of both musculoskeletal as well as neuropathic origin. Pain also expressly includes acute pain or sudden pain. Pain scales for the measurement of pain level are well known, such as those disclosed, for example, in McConnell, S. et al., "The Western Ontario and McMaster Universities Osteoarthritis Index (WOMAC): A Review of Its Utility and Measurement Properties", *Arthritis Care & Research*, 45:453-461, 2001, and Haefeli., M. et al., "Pain Assessment", *European Spine Journal* 2006 January; 15 (Suppl 1): S17-S24.

"Post-surgical pain" (interchangeably termed "post-incisional" or "post-traumatic pain") refers to pain arising or resulting from an external trauma such as a cut, puncture, incision, tear, or wound into tissue of an individual (including that that arises from all surgical procedures, whether invasive or non-invasive). As used herein, post-surgical pain does not include pain that occurs (arises or originates) without an external physical trauma. In some embodiments, post-surgical pain is internal or external (including peripheral) pain, and the wound, cut, trauma, tear or incision may occur accidentally (as with a traumatic wound) or deliberately (as with a surgical incision). As used herein, "pain" includes nociception and the sensation of pain, and pain can be assessed objectively and subjectively, using pain scores and other methods well-known in the art. Post-surgical pain, as used herein, includes allodynia (i.e., increased response to a normally non-noxious stimulus) and hyperalgesia (i.e., increased response to a normally noxious or unpleasant stimulus), which can in turn, be thermal or mechanical (tactile) in nature. In some embodiments, the pain is characterized by thermal sensitivity, mechanical sensitivity and/or resting pain. In some embodiments, the post-surgical pain comprises mechanically-induced pain or resting pain. In other embodiments, the post-surgical pain comprises resting pain. The pain can be primary or secondary pain, as is well-known in the art.

As used interchangeably herein, the term "patient," "subject," and "individual," refers to a human, more particularly, a patient in need thereof. In certain embodiments, the patient is further characterized with a disease, disorder, or condition (e.g., pain, for example, primary or secondary headache and/or migraine including chronic migraine) that would benefit from a reduction in TrkA activity. In another embodiment, the patient is further characterized as being at risk of developing a condition described above, or condition that would benefit from a reduction in TrkA activity.

A pharmaceutically acceptable salt of the compound of the invention can be formed, for example, by reaction of an appropriate free base of a compound of the invention and an appropriate pharmaceutically acceptable acid in a suitable solvent under standard conditions well known in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

A compound of FORMULA I, or a pharmaceutically acceptable salt thereof, or a pharmaceutical composition thereof may be prepared by a variety of procedures known to one of ordinary skill in the art, some of which are illustrated in the preparations and examples below. The products of each step in the preparations and examples below can be recovered by conventional methods well known in the art, including extraction, evaporation, precipitation, chromatography, filtration, trituration, and crystallization. In the preparations and examples below, all substituents unless otherwise indicated, are as previously defined. The reagents and starting materials are readily available to one of ordinary skill in the art. Without limiting the scope of the invention, the following preparations and examples are provided to further illustrate aspects of the invention. In addition, one of ordinary skill in the art appreciates that the compound of FORMULA I may be prepared by using any other suitable starting material or intermediate which can be prepared by one of skill in the art.

Certain abbreviations may be used herein, and have the following meanings unless other wise specified: "aa" refers to amino acid; "ACN" refers to acetonitrile; "Ac" refers to acetyl; "hBDNF" refers to human Brain-derived neurotrophic factor; "CAS #" refers to Chemical Abstracts Registry number; "DCM" refers to methylene chloride or dichloromethane; "DIPEA" refers to N,N-diisopropylethylamine; "DMF" refers to N,N-dimethylformamide; "DMSO" refers to dimethyl sulfoxide; "D-PBS" refers to Dulbecco's phosphate buffered Saline; "EDTA" refers to ethylenediaminetetraacetic acid; "ESMS" and "ES/MS" refer to Electrospray Mass Spectrometry; "Et" refers to ethyl; "Et$_2$O" refers to diethyl ether; "EtOAc" refers to ethyl acetate; "EtOH" refers to ethanol or ethyl alcohol; "h" or "hr" refers to hour or hours; "HATU" refers to 1-[bis(dimethylamino)methylene]-1H-1,2,3-triazolo[4,5-b]pyridinium 3-oxid hexafluorophosphate; "hTrk" refers to human tropomysin receptor kinase; "HPLC" refers to High Performance Liquid Chromatography; "IC$_{50}$" refers to the concentration of an agent that produces 50% of the maximal inhibitory response possible for that agent; "LC-ES/MS" refers to Liquid Chromatography with tandem Electrospray Mass Spectrometry; "min" refers to minute or minutes; "Me" refers to methyl; "MeOH" refers to methanol or methyl alcohol; "min" refers to minute or minutes; "n-BuLi" refers to n-butyllithium; "OAc" refers to acetate or acetoxy; "PBS" refers to phosphate-buffered saline; "RT" refers to room temperature; "SD" refers to standard deviation; "sec" refers to second or seconds as a unit of time; "SEM" refers to standard error of the mean; "SFC" refers to Supercritical Fluid Chromatography; "SH2" refers to Src Homolgy 2 domain; "THF" refers to tetrahydrofuran; "Tris" refers to tris(hydroxymethyl)aminomethane or 2-amino-2-(hydroxymethyl)propane-1, 3-diol; "t$_R$" refers to retention time; "U/mL" refers to units per milliliter; "U2OS" refers to human bone osteosarcoma epithelial cells or cell line; "v/v" refers to volume to volume as a ratio of solvent concentration.

PREPARATIONS AND EXAMPLES

The following Preparations and Examples further illustrate the invention and represent typical synthesis of various compounds of the invention. The reagents and starting materials are readily available, or may be readily synthesized by one of ordinary skill in the art. It should be understood that the Preparations and Examples are set forth by way of illustration and not limitation, and that various modifications may be made by one of ordinary skill in the art.

LC-ES/MS is performed on an AGILENT® HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C18 2.1 mm×50 mm, 3.0µ; gradient: 5-100% B in 3 min, then 100% B for 0.75 min column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: XTERRA® MS C18 columns 2.1×50 mm, 3.5 µm; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1.2 mL/min; Solvent A: 10 mM NH$_4$HCO$_3$ pH 9; Solvent B: ACN; wavelength: 214 nm.

Unless otherwise specified, preparative reversed phase chromatography is performed on an AGILENT® 1200 LC-ES/MS equipped with a Mass Selective Detector mass spectrometer and a LEAP® autosampler/fraction collector. High pH methods are run on a 75×30 mm PHENOMENEX® GEMINI®-NX, 5µ particle size column with a 10×20 mm guard. Flow rate of 85 mL/min. Eluent is 10 mM ammonium bicarbonate (pH 10) in acetonitrile.

NMR spectra are performed on a Bruker AVIII HD 400 MHz NMR Spectrometer, obtained as CDCl$_3$ or (CD$_3$)$_2$SO solutions reported in ppm, using residual solvent [CDCl$_3$, 7.26 ppm; (CD$_3$)$_2$SO, 2.05 ppm] as reference standard.

When peak multiplicities are reported, the following abbreviations may be used: s (singlet), d (doublet), t (triplet), q (quartet), m (multiplet), br-s (broad singlet), dd (doublet of doublets), dt (doublet of triplets). Coupling constants (J), when reported, are reported in hertz (Hz).

Preparation 1

Methyl 2-fluoro-4-(trifluoromethyl)benzoate

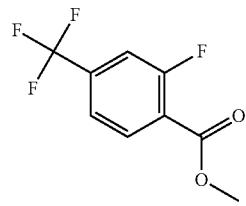

2-Fluoro-4-(trifluoromethyl)benzoic acid (5 g, 23 mmol) is dissolved in MeOH (100 mL) and a concentrated aqueous solution of H$_2$SO$_4$ (200 µL, 4 mmol) is added. The resulting mixture is heated to reflux with stirring for 48 h. The reaction mixture is concentrated under reduced pressure, the residue is diluted with water, and extracted with EtOAc. The organic extracts are washed sequentially with saturated aqueous NaHCO$_3$ and saturated aqueous NaCl, dried over Na$_2$SO$_4$, filtered, and the filtrate is concentrated under reduced pressure to obtain the title compound (5.2 g, 99% yield). $^1$H nmr (CDCl$_3$): δ 3.993 (s, 3H), 7.447 (d, 1H), 7.507 (d, 1H), 8.091 (t, 1H).

Preparation 2

Methyl 2-fluoro-5-nitro-4-(trifluoromethyl)benzoate

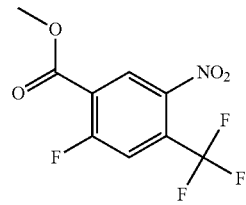 [SMILES: COC(=O)c1cc([N+](=O)[O-])c(C(F)(F)F)cc1F]

Methyl 2-fluoro-4-(trifluoromethyl)benzoate (5.1 g, 23 mmol) is dissolved in concentrated aqueous H$_2$SO$_4$ (25 mL) and the resulting mixture is cooled to 0° C. with stirring. An aqueous solution of 7M HNO₃ (2.5 mL, 40 mmol) is added dropwise over 15 min at 0° C., and the resulting mixture is allowed to warm to RT with stirring for 1 h. The reaction mixture is poured over ice, and the resulting precipitate is collected by filtration, washed with water, and air-dried with vacuum suction. The filtercake is dissolved in EtOAc (100 mL), and the organic mixture is washed sequentially with saturated aqueous NaHCO₃ and saturated aqueous NaCl. The organic extract is dried over Na₂SO₄, filtered, and concentrated under reduced pressure to obtain the title compound (5.8 g, 95% yield) as a yellow solid. ¹H nmr (CDCl₃): δ 4.043 (s, 3H), 7.672 (d, 1H), 8,598 (d, 1H).

Preparation 3

Methyl 5-amino-2-fluoro-4-(trifluoromethyl)benzoate

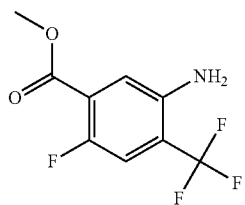

Methyl 2-fluoro-5-nitro-4-(trifluoromethyl)benzoate (5.8 g, 21.7 mml) is dissolved in MeOH (150 mL), and the mixture is sparged with N2. Pd/C (500 mg) is added, the reaction mixture is sealed, and the resulting mixture is stirred under a balloon of H₂ at ambient temperature and pressure for 4 h. The reaction mixture is purged with N2, filtered over a bed of diatomaceous earth, and the methanolic filtrate is concentrated under reduced pressure. The resulting crude residue is purified by chromatography over silica gel, eluting with a gradient of 5-60% EtOAc in hexanes) to obtain the title compound (3.5 g, 68% yield), after evaporation of the desired chromatographic fractions. ESMS (m/z): 236 (M−H).

Preparation 4

Methyl 5-bromo-2-fluoro-4-(trifluoromethyl)benzoate

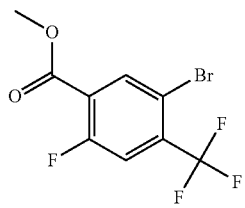 [SMILES: COC(=O)c1cc(Br)c(C(F)(F)F)cc1F]

CuBr₂ (3.15 g, 14.1 mmol) and isoamylnitrite (2.2 mL, 16 mmol) are added to a solution of methyl 5-amino-2-fluoro-4-(trifluoromethyl)benzoate (3 g, 12.7 mmol) dissolved in ACN (30 mL) and the resulting mixture is stirred at RT for 2 h. The reaction mixture is diluted with hexanes, filtered through a bed of diatomaceous earth, and the collected filtrate is concentrated under reduced pressure. The resulting residue is purified by chromatography over silica gel, eluting with a gradient of 5-40% EtOAc in hexanes, to obtain the title compound (3.8 g, 71% yield) after evaporation of the desired chromatographic fractions. ¹H nmr (CDCl₃): δ 3.996 (s, 3H), 7.521 (dd, 1H), 8.272 (t, 1H).

Preparation 5

Methyl 2-fluoro-5-(1-methylpyrazol-3-yl)-4-(trifluoromethyl)benzoate

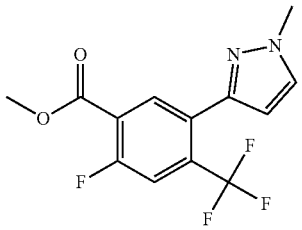 [SMILES: COC(=O)c1cc(-c2ccn(C)n2)c(C(F)(F)F)cc1F]

1-Methyl-3-(4,4,5,5-tetramethyl-1,3,2-dioxaborolan-2-yl)-1H-pyrazole (1.0 g, 4.8 mmol) and methyl 5-bromo-2-fluoro-4-(trifluoromethyl)benzoate (1.3 g, 4.3 mmol) are suspended in THF (6 mL) containing 1M aqueous K₃PO₄ (2 mL, 2 mmol) in a microwave vial equipped with a stir bar and the mixture is sparged with N2 for 5 min. Methanesulfonato(2-dicyclohexylphosphino-2',4',6'-tri-iso-propyl-1,1'-biphenyl)(2'-methylamino-1,1'-biphenyl-2-yl)palladium (II) (190 mg, 0.2 mmol) is added and the vial is sealed with a Teflon cap. The resulting mixture is irradiated in a microwave reactor at 100° C. for 4 h. The reaction mixture is cooled to RT and loaded directly onto silica gel for purification, eluting with a gradient of 5-100% MeOH (containing 10% v/v 2 M NH₃ in MeOH) in DCM to obtain, after evaporation of the desired chromatographic fractions, the title compound (1.1 g, 85% yield) as a white solid. ESMS (m/z): 303 (M+H).

Preparation 6

2-fluoro-5-(1-methylpyrazol-3-yl)-4-(trifluoromethyl)benzoic acid

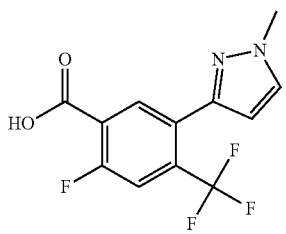 [SMILES: Cn1ccc(-c2cc(C(=O)O)c(F)cc2C(F)(F)F)n1]

Solid LiOH (1.0 g, 41 mmol) is added to a solution of methyl 2-fluoro-5-(1-methylpyrazol-3-yl)-4-(trifluoromethyl)benzoate (1.1 g, 3.7 mmol) in EtOH (50 mL) and H₂O (10 mL) and the resulting reaction mixture is stirred at RT for 2 h. The mixture is acidified with 5N HCl and extracted with EtOAc. The organic extracts are washed with saturated aqueous NaCl, dried over Na₂SO₄, filtered, and concentrated under reduced pressure to obtain the title compound (1.1 g, 99% yield) as a white solid. ESMS (m/z): 298 (M+H).

Preparation 7

5-bromo-4-iodo-pyridine-3-carboxylic acid hydrochloride

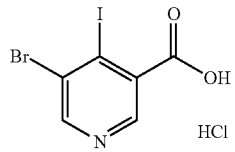

A mixture of THF (350 mL) and 2,2,6,6-tetramethylpiperidine (41 mL, 240 mmol) is cooled with stirring to −50° C. under N2. A 2.5 M solution of n-BuLi in hexanes (81 mL, 220 mmol) is added portion wise, maintaining temperature below −40° C., and the resulting mixture is stirred at −50° C. for 10 min. 5-Bromopyridine-3-carboxylic acid (20.0 g, 99.0 mmol) is added portion wise, maintaining temperature below −40° C. The resulting reaction mixture is stirred at −50° C. and added to a solution of 12 (30.2 g, 119 mmol) in THF (300 mL) via cannula under N2 with slight pressure at −50° C. with stirring. The resulting mixture is warmed to RT with stirring under N2 for 4 h. The reaction mixture is quenched with water (20 mL), and most of the solvent is evaporated under a stream of N2. The resulting residue is poured into 1 N aqueous solution of NaOH (250 mL). The resulting basic mixture is washed with Et$_2$O:EtOAc (1:1, ~250 mL), and the separated aqueous layer is acidified to pH ~1 with 5 N aqueous HCl. The resulting precipitate is collected by filtration, triturated with MeOH, collected by filtration, and the filter cake is washed with Et$_2$O and hexanes and air-dried, to obtain the title compound (20.0 g, 55% yield) as a tan solid, sufficient for use without additional purification and used as is in the next step. ESMS (m/z): ($^{79}$Br/$^{81}$Br) 328/330 (M+H).

Preparation 8

Methyl 5-bromo-4-iodo-pyridine-3-carboxylate

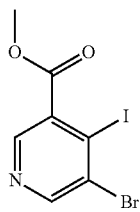

In a 50 mL RBF is added 5-bromo-4-iodo-pyridine-3-carboxylic acid (2.8 g, 8.5 mmol), acetone (23 mL), K$_2$CO$_3$ (1.8 g, 12.8 mmol), and dimethyl sulfate (891 µL, 9.3 mmol). The mixture is allowed to stir at RT overnight. The reaction mixture is filtered through diatomaceous earth, rinsed with acetone and EtOAc, and the filtrate is concentrated under reduced pressure. The resulting residue is purified by flash chromatography on silica gel, eluting with a gradient of 0-100% EtOAc (containing 2% Et$_3$N) in isohexane, to give the title compound (2.15 g, 70.5% yield) as crystalline yellow solid after evaporation of the desired chromatographic fractions. $^1$H nmr ((CD$_3$)$_2$SO): δ 3.906 (s, 3H), 8.592 (s, 1H), 8.862 (s, 1H).

Preparation 9

Methyl 5-bromo-4-(2-pyridyl)pyridine-3-carboxylate

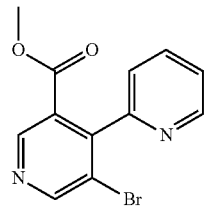 [SMILES: COC(=O)c1cncc(Br)c1-c1ccccn1]

References: *Bioorg. Med. Chem. Lett.*, 2017, 27(16), 3817; *Bioorg. Med. Chem. Lett.*, 2016, 26(1), 160.

A 25 mL microwave vessel containing, methyl 5-bromo-4-iodo-pyridine-3-carboxylate (710 mg, 2.1 mmol), CsF (630 mg, 4.1 mmol), LiCl (176 mg, 4.1 mmol), tetrakis (triphenyl-phosphine)palladium(0) (120 mg, 0.1 mmol) is evacuated and purged with nitrogen (two cycles of vacuum/nitrogen). 1,4-Dioxane (18 mL, 210.8 mmol) is added, nitrogen bubbled through the mixture, and tributyl(2-pyridyl)stannane (540 µL, 1.7 mmol) is added. The sealed reaction mixture is heated to 125° C. in a heating block and heated overnight. The resulting mixture is stirred over 48 h at RT. The crude mixture is filtered through diatomaceous earth and rinsed with EtOAc, and the filtrate is concentrated under reduced pressure. The resulting residue is purified by flash chromatography over silica gel, eluting with 0 to 70% EtOAc in isohexanes, to obtain the title compound (140 mg, 23% yield) as a golden oil after evaporation of the desired chromatographic fractions. ESMS (m/z): ($^{79}$Br/$^{81}$Br) 292/294 (M+H).

Preparation 10

2-fluoro-5-(1-methylpyrazol-3-yl)-4-(trifluoromethyl)benzamide

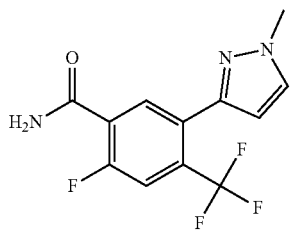 [SMILES: Cn1ccc(-c2cc(C(N)=O)c(F)cc2C(F)(F)F)n1]

2-Fluoro-5-(1-methylpyrazol-3-yl)-4-(trifluoromethyl) benzoic acid (33.1 g, 115 mmol), NH$_4$Cl (8.0 g, 150 mmol), HATU (57 g, 142.4 mmol), DIPEA (44 mL, 252 mmol) and DMF (300 mL) are combined in a round-bottomed flask and stirred at RT for 1 h. The reaction mixture is diluted with water and the resulting precipitate is collected by filtration, washed with water, and dried under vacuum at 50° C. to obtain the title compound (24 g, 72% yield) as an off-white, crystalline solid. The filtrate is concentrated under reduced pressure and diluted with water. The resulting mixture is extracted with EtOAc, and the organic layer is washed with saturated aqueous NaCl, dried over Na$_2$SO$_4$, filtered, and concentrated under reduced pressure. The resulting residue is triturated with EtOAc, collected by filtration and air-dried, to obtain additional title compound (5.4 g, 16% yield) as a white, crystalline solid. The title compound is combined with previously recovered title material (29.0 g, 92% total yield). ESMS (m/z): 288 (M+H).

Preparation 11

Methyl 5-[[2-fluoro-5-(1-methylpyrazol-3-yl)-4-(trifluoromethyl)benzoyl]amino]-4-(2-pyridyl)pyridine-3-carboxylate

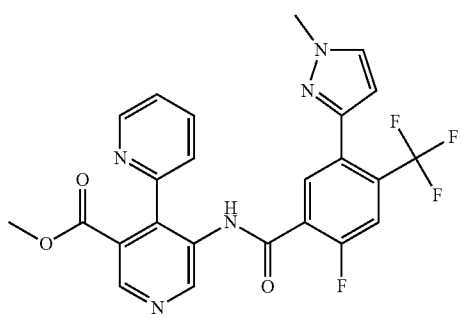 [SMILES: COC(=O)c1cncc(NC(=O)c2cc(-c3ccn(C)n3)c(C(F)(F)F)cc2F)c1-c1ccccn1]

A 25 mL microwave vial is charged with, 2-fluoro-5-(1-methylpyrazol-3-yl)-4-(trifluoromethyl)benzamide (282 mg, 1 mmol), $CsCO_3$ (800 mg, 2.5 mmol), tris(dibenzylideneacetone)dipalladium(0) (150 mg, 0.2 mmol) and 4,5-bis(diphenylphosphino)-9,9-dimethylxanthene (190 mg, 0.3 mmol). The vial is sealed, subjected to two cycles of vacuum/nitrogen, and a solution of methyl 5-bromo-4-(2-pyridyl)pyridine-3-carboxylate (240 mg, 0.8 mmol) in 1,4-dioxane (8 mL) is added. Nitrogen is bubbled through the mixture for 5 min and mixture is heated in a heating block at 130° C. overnight. The mixture is filtered through diatomaceous earth and rinsed sequentially with EtOAc and MeOH, and the filtrate is concentrated to give a brown oil. The resulting residue is diluted in MeOH (to a total volume of 8.5 ml), filtered over a bed of diatomaceous earth, and purified by preparative HPLC over C18 silica gel (PHENOMENEX® Gemini, 5μ, 30×100 mm, 60 mL/min, 210 nm), eluting with a gradient of 5-100% ACN in water containing 10 mM $NH_4CO_3$, adjusted to pH ~9 with aqueous $NH_4OH$, over 9 minutes (1 total injection), to obtain the title compound (40 mg, 8.5% yield) after evaporation of the desired chromatographic fractions. ESMS (m/z): 500 (M+H).

Preparation 12

5-[[2-fluoro-5-(1-methylpyrazol-3-yl)-4-(trifluoromethyl)benzoyl]amino]-4-(2-pyridyl)pyridine-3-carboxylic acid

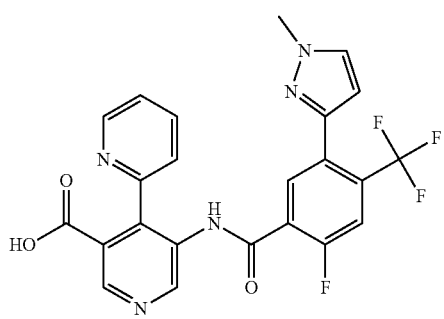 [SMILES: Cn1ccc(-c2cc(C(=O)Nc3cncc(C(=O)O)c3-c3ccccn3)c(F)cc2C(F)(F)F)n1]

Methyl 5-[[2-fluoro-5-(1-methylpyrazol-3-yl)-4-(trifluoromethyl)benzoyl]amino]-4-(2-pyridyl)pyridine-3-carboxylate (40 mg, 0.07 mmol) is dissolved in MeOH (5 mL) and treated with a 2M aqueous solution of NaOH (5 mL, 10 mmol), and the resulting mixture is stirred at for 30 min. The reaction is acidified with an aqueous solution of 2M HCl and extracted with DCM. The organic layer is separated, dried through a hydrophobic frit, and concentrated under reduced pressure to give a pale yellow solid. The aqueous phase is additionally extracted with 20% MeOH/DCM, the layers are separated, and the organic extract is dried over $MgSO_4$, filtered, combined with previous organic phase, and concentrated to give the title compound (40 mg, 118% crude yield) as a pale yellow solid suitable for use without additional purification. ESMS (m/z): 486 (M+H).

Example 1

5-[[2-fluoro-5-(1-methylpyrazol-3-yl)-4-(trifluoromethyl)benzoyl]amino]-4-(2-pyridyl)pyridine-3-carboxamide

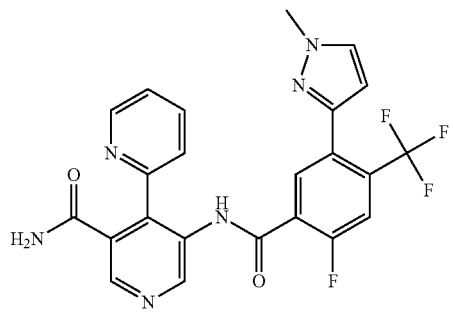 [SMILES: Cn1ccc(-c2cc(C(=O)Nc3cncc(C(N)=O)c3-c3ccccn3)c(F)cc2C(F)(F)F)n1]

5-[[2-fluoro-5-(1-methylpyrazol-3-yl)-4-(trifluoromethyl)benzoyl]amino]-4-(2-pyridyl)pyridine-3-carboxylic acid (40 mg, 0.08 mmol) is dissolved in anhydrous DMF (2 mL). HATU (58 mg, 0.2 mmol) and $NH_4Cl$ (55 mg, 1.0 mmol), and DIPEA (270 μL, 1.6 mmol) are added. The reaction mixture is stirred at RT for 60 min, diluted in MeOH (to a total volume of 6 mL), filtered over diatomaceous earth, and purified by preparative HPLC (PHENOMENEX® Gemini 5μ, 30×100 mm, 60 mL/min, 220 nm) over C18 silica gel, eluting with a gradient of 15-100% ACN in water containing 10 mM $NH_4CO_3$, adjusted to pH ~9 with aqueous $NH_4OH$ over 9 minutes, to obtain the title compound (25 mg, 56% yield) after evaporation of the desired chromatographic fractions. ESMS (m/z): 485 (M+H).

Assays

Human Tropomyosin Receptor Kinase (hTrkA, hTrkB, hTrkC) Assays to Examine hTrk Kinase Inhibitors The reaction of non-phosphorylated hTrk kinase domains (hTrkA, aa: 441-796, hTrkB, aa: 526-838 or hTrkC, aa: 510-825) with a fluorescein-labeled poly-GT substrate (poly-GT, Invitrogen) generates a fluorescein-labeled phosphorylated product. Binding of the terbium-labeled antibody (Invitrogen) to the phosphorylated tyrosine product brings the terbium and fluorescein into proximity, resulting in an increase in time-resolved fluorescence resonance energy transfer (TR-FRET). In the presence of an inhibitor, formation of phosphorylated product is reduced, and the TR-FRET value is decreased.

Inhibition of hTrk kinase activity: The activity of human tropomyosin receptor hTrk kinase is quantitated using TR-FRET technology (Invitrogen) as per vendor instructions. Briefly, compounds for dose-response studies are serially diluted in dimethyl sulfoxide (1:2 for 20 concentrations) using an acoustic dispensing instrument Echo Access (Labcyte) and dispensed into ProxiPlate-384 plus plates (PerkinElmer). Kinase domain for hTrkA, hTrkB or hTrkC is added and the plates are incubated at room temperature (RT) for one hour. ATP and poly-GT are next added and plates are incubated at RT for one hour. EDTA and terbium-labeled antibody are added and plates are incubated at RT for one hour after which the TR-FRET signal is detected using an ENVISION® plate reader (Perkin-Elmer). The ratio of fluorescence at 520 to 495 nm is calculated.

Data Analysis: The data are converted into % Inhibition and relative IC50 values are calculated from the top-bottom range of the concentration response curve using a four-parameter logistic curve fitting program (GENEDATA SCREENER® v13.0.5) with the equation $Y=Bottom+(Top-Bottom)/(1+10^{((Log\ IC_{50}-X)*HillSlope)})$. The top of the curve is 100% inhibition and defined by the kinase wells treated with an internal standard, which is a non-selective hTrk kinase inhibitor ([final]=7.9 uM), whereas the bottom of the curve is 0% inhibition and defined by the kinase wells in the absence of compound.

The internal standard used in this procedure is N-[5-[7-[(1S)-2-hydroxy-1-methyl-ethyl]pyrrolo[2,3-d]pyrimidine-5-carbonyl]-3-pyridyl]-2-[4-(trifluoromethyl)phenyl]acetamide:

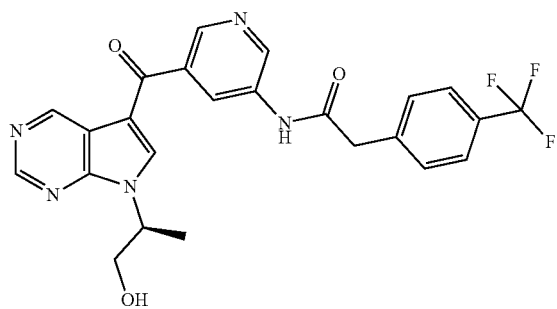 [SMILES: C[C@@H](CO)n1cc(C(=O)c2cncc(NC(=O)Cc3ccc(C(F)(F)F)cc3)c2)c2cncnc21]

This internal standard is commercially available as CAS Registry Number 1402438-37-2. This internal standard may also be made using the teachings of U.S. Pat. No. 8,846,698.

In Vitro Inhibition of SH2 Domain Protein Recruitment in Human Bone Osteosarcoma Epithelial Cells by Human Tropomyosin Receptor Kinase (hTrk) Inhibitors Activation of hTrkA, TrkB or TrkC is examined using PathHunter® (DiscoverX) enzyme fragment complementation technology. In this approach, one fragment of β-galactosidase (β-gal) ProLink (PK) is fused to the C-terminal of the Trk receptor and co-expressed with a phosphotyrosine SH2 domain protein fused with the remaining fragment of β-gal, Enzyme Acceptor (EA), in human Bone Osteosarcoma Epithelial (hU2OS) cells also expressing the p75 neurotrophic receptor (DiscoverX). Activation of hTrk receptors by agonists results in receptor phosphorylation. The SH2-EA fusion protein binds the phosphorylated hTrk receptor resulting in complementation of PK and EA to form an active β-gal enzyme. β-gal enzymatic activity is quantitatively measured using a chemiluminescent substrate in the PathHunter® detection kit (DiscoverX). Human nerve growth factor (hNGF, PeproTech), human brain-derived neurotrophic factor (hBDNF, PeproTech) and recombinant human neurotrophin-3 protein (hNT-3, PeproTech) are used as agonists for hTrkA, hTrkB or hTrkC receptors respectively.

Cell Culture: Cultured hU2OS cells that express hTrk receptors and p75 (PathHunter® system, DiscoverX) are grown in AssayComplete™ U2OS Cell Culture Kit 11 (DiscoverX) to about 80% confluence. On the day before the assay, cells are detached using AssayComplete™ Cell Detachment Reagent (DiscoverX), harvested in AssayComplete™ Cell Plating 16 Reagent (DiscoverX) to the correct cell concentration (250,000/ml) and seeded at 5K/well into 384-well poly-D-lysine coated white plates (BD Biosciences). Cell plates are incubated at 37° C. overnight.

Inhibition of hTrk kinase activity: The activity of hTrkA and hTrkC kinase is quantitated using Pathhunter® technology (DiscoverX) as per vendor instructions.

Briefly, on the assay day, compounds for dose-response studies are serially diluted in dimethyl sulfoxide (1:3 for 10 concentrations) using an acoustic dispensing instrument Echo Access (Labcyte) and dispensed into cell plates that are subsequently incubated at room temperature (RT) for one hour. For studies in hTrkA-p75 cells, recombinant human NGF-β (PeproTech) is added to the cells at an ECK) concentration ([final]=27 ng/ml) and plates are incubated at RT for three hours. Pathhunter® detection reagents (DiscoverX) are added and plates are read in an ENVISION® plate reader (Perkin-Elmer) at 700 nm after 1 h incubation at RT in the dark. Human brain-derived neurotrophic factor (hBDNF, PeproTech, [final]=20 ng/ml) or recombinant human neurotrophin-3 protein (hNT-3, PeproTech, [final]=29 ng/ml) are used as agonist for studies in hTrkB-p75 or hTrkC-p75 cells, respectively.

Data Analysis: The data are converted into % Inhibition and relative $IC_{50}$ values are calculated from the top-bottom range of the concentration response curve using a four-parameter logistic curve fitting program (GENEDATA SCREENER® v13.0.5) with the equation $Y=Bottom+(Top-Bottom)/(1+10^{((Log\ IC_{50}-X)*HillSlope)})$. The top of the curve is 100% inhibition and defined by the wells without agonist stimulation. The bottom of the curve is 0% inhibition and defined by the agonist-stimulated (hNGF, hBDNF or hNT) wells in the absence of inhibitor.

TABLE 1

| Relative $IC_{50}$ in nM of Example 1 against hTrkA/B/C ± SEM (N = number of times tested) | | | | | |
|---|---|---|---|---|---|
| PathHunter® cell-based assay | | | Binding Assays | | |
| hTrkA (nM) | hTrkB (nM) | hTrkC (nM) | hTrkA (nM) | hTrkB (nM) | hTrkC (nM) |
| 1.24 (N = 32) | 6,700 (N = 25) | 9,010 (N = 24) | 1.09 (N = 4) | >4,290 (N = 1) | 8,360 (N = 1) |

These data indicate that the compound of Example 1 is a potent inhibitor of and selective for hTrkA in vitro.

Preparation of Hemi Succinic Acid Cocrystal Formation of Example 1

To a flask, add 16 g of the compound of Example 1 (33.0 mmol, 1 eq). Add THF (288 mL) and water (32 mL). Heat this mixture to 55° C. and obtain a solution. Polish filter the solution and rinse with 9:1 v:v THF:water (2×16 mL). In a separate flask, add succinic acid (3.9 g, 33.0 mmol, 1 eq) and ethanol (80 mL). Mix until a solution results.

Transfer the solution of the compound of Example 1 to a flask with overhead stirring and a distillation head and rinse with 9:1 v:v THF:water (16 mL). Add the succinic acid solution in EtOH. Heat the solution to reflux and begin distillation. After 300 mL distillate are collected, solids crystallize from the mixture. Add back EtOH (160 mL) and stir. Turn off the heat. Cool to room temperature. Filter and rinse with EtOH (4×16 mL). Dry the wetcake under vacuum at 50° C. Isolate white solids, the hemi succinic acid salt of the compound of Example 1 (16.58 g, 30.5 mmol, 92.5% yield).

Co-Crystal Formation

The following is a description of a crystallization process for the hemi succinic acid cocrystal. Those skilled in the art would appreciate that a similar process could be used to crystallize the free base (with modifications as needed, as would be appreciated by a skilled artisan).

To a flask, add the hemi succinic acid cocrystal of Example 1 (40.1 g, 72.2 mmol, 1 eq). Add DMSO (120 mL), and heat to 50° C. to obtain a solution. Polish filter the solution and rinse with DMSO (2×~2 mL).

To another flask, add succinic acid (14.5 g, 123 mmol, 1.7 eq) and EtOH (980 mL). Mix until a solution results.

To the crystallization vessel, add DMSO (20 mL) and a portion of the succinic acid solution in EtOH (140 mL). Heat to 50° C. Add seed crystals of the hemi succinic acid salt of the compound of Example 1 (1.4 g) and stir.

Add the solution of compound of Example 1 in DMSO and the solution of succinic acid in EtOH to the crystallization vessel in separate feed streams over 4 hours, maintaining the temperature of the crystallization vessel at 50° C. After the co-addition is complete, cool the mixture slowly to 20° C. Stir at 20° C., then filter and rinse with a solution of succinic acid in EtOH (2 mg/mL succinic acid in EtOH, 4×70 mL rinses). Dry the wetcake under vacuum at 50° C. Isolate white solids, the hemi succinic acid cocrystal of the compound of Example 1 (38.2 g, 70.3 mmol, 92% yield corrected for the seed amount).

NMR: $^1$H NMR (400 MHz, DMSO-$d_6$) δ 12.14 (s, 1H), 10.66 (d, J=3.1 Hz, 1H), 9.08 (s, 1H), 8.70-8.63 (m, 1H), 8.61 (s, 1H), 8.06 (s, 1H), 7.94-7.85 (m, 2H), 7.83 (d, J=10.6 Hz, 1H), 7.80 (d, J=2.2 Hz, 1H), 7.60-7.52 (m, 2H), 7.46-7.38 (m, 1H), 6.46-6.41 (m, 1H), 3.93 (s, 3H), 2.43 (s, 2H).

Mass spec: found 485.0 m/z, theory 485.1

X-Ray Powder Diffraction (XRPD) of Crystalline Forms

The XRPD patterns of crystalline solids are obtained on a Bruker D8 Endeavor X-ray powder diffractometer, equipped with a CuKα (1.5418 Å) source and a Linxeye detector, operating at 40 kV and 40 mA. The sample is scanned between 4 and 42 2θ°, with a step size of 0.009 2θ° and a scan rate of 0.5 seconds/step, and using 0.3° primary slit opening, and 3.9° PSD opening. The dry powder is packed on a quartz sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standard with peaks at 8.853 and 26.774 2θ°. It is well known in the crystallographic art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of ±0.2 2θ° is presumed to take into account these potential variations without hindering the unequivocal identification of the indicated crystal form. Confirmation of a crystal form may be made based on any unique combination of distinguishing peaks.

XRPD of Hemisuccinic Acid Form of Example 1 (3848608) RS7-H81933-069A

A prepared sample of the hemisuccinic acid of Example 1 is characterized by an XRPD pattern using CuKα radiation as having diffraction peaks (2-theta values) as described in Table A below, and in particular having a peak at 10.5 in combination with one or more of the peaks selected from the group consisting of 12.6, and 22.2; with a tolerance for the diffraction angles of 0.2 degrees.

TABLE A

XRPD peaks of crystalline hemisuccinic acid of Example 1 hemisuccinic acid of Example 1

| Peak | Angle (°2-Theta) +/− 0.2° | Relative Intensity (% of most intense peak) |
|---|---|---|
| 1 | 10.5 | 100.0% |
| 2 | 11.8 | 33.6% |
| 3 | 12.6 | 37.2% |
| 4 | 14.1 | 34.4% |
| 5 | 16.0 | 32.2% |
| 6 | 18.6 | 36.5% |
| 7 | 20.6 | 42.0% |
| 8 | 21.3 | 54.3% |
| 9 | 22.2 | 67.1% |
| 10 | 24.7 | 69.5% |

COMPARATIVE EXAMPLES

The following two molecules were made from U.S. Pat. No. 9,815,846 using the methods and procedures described in that patent. Specifically, Examples 89 and 141 of U.S. Pat. No. 9,815,846 were prepared and have the following structures:

Example 89 of U.S. Pat. No. 9,815,846

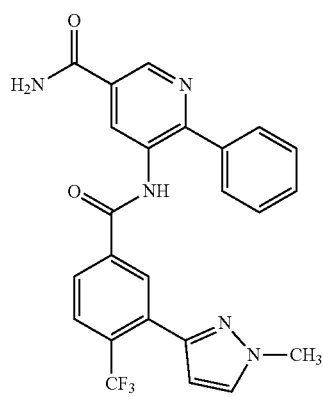 [SMILES: Cn1ccc(-c2cc(C(=O)Nc3cc(C(N)=O)cnc3-c3ccccc3)ccc2C(F)(F)F)n1]

Example 141 of U.S. Pat. No. 9,815,846

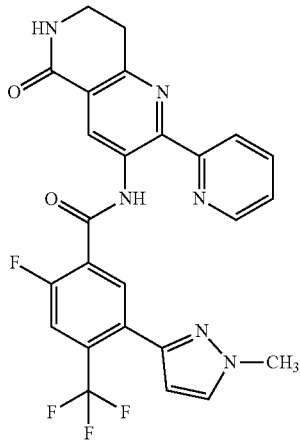 [SMILES: Cn1ccc(-c2cc(C(=O)Nc3cc4c(nc3-c3ccccn3)CCNC4=O)c(F)cc2C(F)(F)F)n1]

These two compounds from U.S. Pat. No. 9,815,846 were run in the Assays (which procedures were outlined above) in order to determine their binding of Trk A, Trk B and Trk C. The data is shown below in Table 2 (and is compared to the data for Example 1 found in Table 1 above)).

TABLE 2

Comparative IC50 data for binding to Trk A, Trk B, and Trk C.

|  | Example 89 of US Patent No. 9815846 | Example 141 of US Patent No. 9815846 | Example 1 of the present disclosure (data taken from Table 1 above) |
|---|---|---|---|
| hTrkA IC50 | 1.55 nM | 11.1 nM | 1.24 nM |
| hTrkB IC50 | 713 nM | >47,900 nM | 6,700 nM |
| hTrkC IC50 | 452 nM | 37,800 nM | 9,010 nM |

As can see from the data in Table 2, the compound of Example 1 is a potent binder of Trk A, and is selective for Trk A. Example 89 of U.S. Pat. No. 9,815,846 is potent with respect to Trk A, but is not as selective for Trk B and Trk C as in Example 1. Example 141 of U.S. Pat. No. 9,815,846 has similar selectivity for Trk A over Trk B and Trk C, but is less potent at the target Trk A. However, it should be noted that the compound of Example 141 of U.S. Pat. No. 9,815,846 in which there is a two pyridine rings is difficult to achieve synthetically, and it would likely not be possible to make this molecule on a kilogram scale using the techniques outlined in U.S. Pat. No. 9,815,846. In fact, the following article shows the difficulty of creating this type of two-pyridine system:

Xinlan A. F. Cook, Antoine de Gombert, Janette McKnight, Loïc R. E. Pantaine and Michael C. Willis, "The 2-Pyridyl Problem: Challenging Nucleophiles in Cross-Coupling Arylations", *Angew. Chem. Int. Ed.* 2020, 59, 2-26.

Further, in examining U.S. Pat. No. 9,815,846, Example 152 has the following structure:

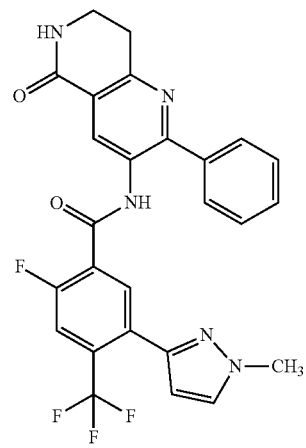 [SMILES: Cn1ccc(-c2cc(C(=O)Nc3cc4c(nc3-c3ccccc3)CCNC4=O)c(F)cc2C(F)(F)F)n1]

The difference between Example 152 and Example 141 of U.S. Pat. No. 9,815,846 is that Example 141 has a pyridine ring whereas Example 152 has a phenyl ring. If you compare the listed Trk A IC50 values for these two molecules that are found in Table 2 of U.S. Pat. No. 9,815,846, Example 141 (with the pyridine ring) has a listed value of 14 nM whereas Example 152 (with the phenyl ring) has a listed value of 0.069 nM. Thus, by using a phenyl ring in Example 152 (rather than a pyridine ring of Example 141), there is a dramatic effect on the potency at TrkA—over 200 fold (e.g., 14 divided by 0.069. is 202.9). However, when compared with the molecule of present Example 1 (which also has a pyridine ring like Example 141 of U.S. Pat. No. 9,815,846), the present Example 1 has good the potency and selectivity.

We claim:
1. A compound of the Formula:

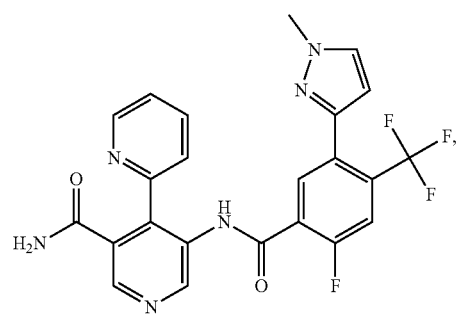 [SMILES: Cn1ccc(-c2cc(C(=O)Nc3cncc(C(N)=O)c3-c3ccccn3)c(F)cc2C(F)(F)F)n1]

or a pharmaceutically acceptable salt thereof.
2. The compound according to claim 1 which is:

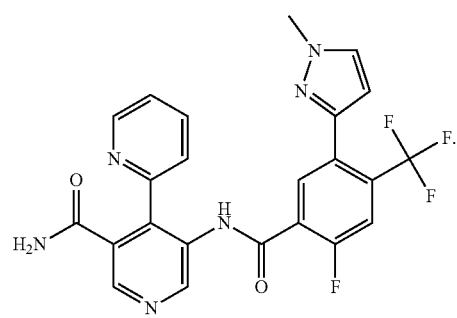 [SMILES: Cn1ccc(-c2cc(C(=O)Nc3cncc(C(N)=O)c3-c3ccccn3)c(F)cc2C(F)(F)F)n1]

3. A pharmaceutical composition comprising a compound according to claim 1, or a pharmaceutically acceptable salt thereof, and one or more pharmaceutically acceptable carriers, diluents or excipients.

4. A pharmaceutical composition comprising a compound according to claim 2 and one or more pharmaceutically acceptable carriers, diluents or excipients.

5. A method of treating pain comprising administering to a patient in need thereof an effective amount of a compound according to claim 1, or pharmaceutically acceptable salt thereof.

6. The method of claim 5, wherein the pain is selected from the group consisting of post-surgical pain, neuropathic pain, rheumatoid arthritis pain and osteoarthritis pain.

7. The method of claim 5, wherein the pain is chronic pain.

8. A method of treating pain comprising administering to a patient in need thereof the composition of claim 3.

9. The method of claim 8, wherein the pain is selected from the group consisting of post-surgical pain, neuropathic pain, rheumatoid arthritis pain and osteoarthritis pain.

10. The method of claim 8, wherein the pain is chronic pain.

11. A compound according to claim 1, or a pharmaceutically acceptable salt thereof, for use in the treatment of pain.

12. The compound for use in the treatment of pain according to claim 11, wherein the pain is selected from the group consisting of post-surgical pain, neuropathic pain, rheumatoid arthritis pain and osteoarthritis pain.

13. The compound for use in the treatment of pain according to claim 11, or a pharmaceutically acceptable salt thereof, wherein the pain is chronic pain.

14. A process for preparing a pharmaceutical composition, comprising admixing a compound according to claim 1, or a pharmaceutically acceptable salt thereof, with one or more pharmaceutically acceptable carriers, diluents, or excipients.

15. A compound which is a hemisuccinic acid salt of the following structure:

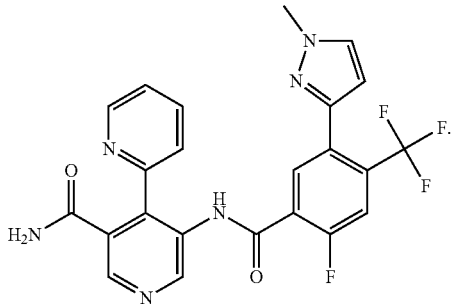 [SMILES: Cn1ccc(-c2cc(C(=O)Nc3cncc(C(N)=O)c3-c3ccccn3)c(F)cc2C(F)(F)F)n1]

16. The hemisuccinic acid salt according to claim 15 which is crystalline.

17. The hemisuccinic acid salt according to claim 16 which is characterized by a substantial peak in the X-ray diffraction spectrum, at diffraction angle 2-theta of 10.5° in combination with one or more of the peaks selected from the group consisting of 12.6, and 22.2; with a tolerance for the diffraction angles of 0.2 degrees.

18. A pharmaceutical composition comprising a compound according to either claim 15 and one or more pharmaceutically acceptable carriers, diluents or excipients.

19. A method of treating pain comprising administering to a patient in need thereof an effective amount of a compound according to either claim 15.

20. The method of claim 19, wherein the pain is selected from the group consisting of post-surgical pain, neuropathic pain, rheumatoid arthritis pain and osteoarthritis pain.

21. The method of claim 19, wherein the pain is chronic pain.

* * * * *